US012611552B2

(12) United States Patent
Zhang et al.

(10) Patent No.: US 12,611,552 B2
(45) Date of Patent: Apr. 28, 2026

(54) METHODS AND SYSTEMS FOR RADIATION THERAPY GUIDANCE

(71) Applicant: SHANGHAI UNITED IMAGING HEALTHCARE CO., LTD., Shanghai (CN)

(72) Inventors: Xinyue Zhang, Shanghai (CN); Zhidu Zhang, Shanghai (CN); Hanyi Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 548 days.

(21) Appl. No.: 18/148,405

(22) Filed: Dec. 29, 2022

(65) Prior Publication Data

US 2023/0398376 A1     Dec. 14, 2023

(30) Foreign Application Priority Data

Jun. 8, 2022    (CN) .......................... 202210642270.7

(51) Int. Cl.
*A61N 5/10*          (2006.01)
*G06T 7/00*          (2017.01)
                            (Continued)

(52) U.S. Cl.
CPC .......... *A61N 5/1049* (2013.01); *G06T 7/0016* (2013.01); *G06T 7/30* (2017.01);
                            (Continued)

(58) Field of Classification Search
CPC .......... A61N 5/1049; A61N 2005/1059; A61N 5/1037; A61N 5/103; A61N 5/1039;
                            (Continued)

(56) References Cited

U.S. PATENT DOCUMENTS

| | | | |
|---|---|---|---|
| 10,376,714 B2 * | 8/2019 | Bharat ................... | A61N 5/107 |
| 2005/0251029 A1 * | 11/2005 | Khamene .............. | G16H 20/30 |
| | | | 382/132 |

(Continued)

FOREIGN PATENT DOCUMENTS

| | | |
|---|---|---|
| CN | 103340646 A | 10/2013 |
| CN | 106932829 A | 7/2017 |

(Continued)

OTHER PUBLICATIONS

First Office Action in Chinese Application No. 202210642270.7 mailed on Apr. 10, 2024, 12 pages.

(Continued)

*Primary Examiner* — Henok Shiferaw
*Assistant Examiner* — Dion J Satcher
(74) *Attorney, Agent, or Firm* — METIS IP LLC

(57) ABSTRACT

The embodiments of the present disclosure provide a method for radiation therapy guidance. The method may include obtain first surface data of a target object to be treated by using an optical camera, wherein the first surface data may reflect the body surface condition of the target object before a treatment fraction; obtain a historical anatomical image of the target object; and determine whether an anatomical image of the target object needs to be reshot for the treatment fraction based on the historical anatomical image and the first surface data.

17 Claims, 7 Drawing Sheets

600

(51) Int. Cl.
   *G06T 7/30*                (2017.01)
   *G06T 7/73*                (2017.01)
(52) U.S. Cl.
   CPC ........ *G06T 7/74* (2017.01); *A61N 2005/1059*
         (2013.01); *G06T 2207/30096* (2013.01)
(58) Field of Classification Search
   CPC ................ A61N 5/1045; A61N 5/1048; A61N
                2005/105; A61N 2005/1052; A61N
                2005/1054; A61N 2005/1055; A61N
                2005/1058; A61N 2005/1061; G06T
                7/0016; G06T 7/30; G06T 7/74; G06T
                2207/30096; G06T 2207/10028; G06T
                2207/20084; G06T 2207/10081; G06T
                       2207/10116; A61B 6/03
   USPC ................................................. 382/103, 382
   See application file for complete search history.

(56)                    References Cited

U.S. PATENT DOCUMENTS

| | | | |
|---|---|---|---|
| 2017/0042489 A1 | 2/2017 | Boyd et al. | |
| 2017/0326385 A1* | 11/2017 | Fishman | A61N 5/1077 |
| 2018/0369611 A1* | 12/2018 | Owens | A61N 5/1049 |
| 2019/0080459 A1* | 3/2019 | Lachaine | A61N 5/1049 |
| 2019/0099619 A1* | 4/2019 | Maltz | A61N 5/1039 |
| 2019/0220986 A1* | 7/2019 | Magro | A61B 6/032 |
| 2019/0232087 A1* | 8/2019 | Cordero Marcos | A61N 5/1038 |
| 2021/0154494 A1* | 5/2021 | Maurer | G06N 20/00 |
| 2021/0390696 A1* | 12/2021 | Iwase | A61B 3/102 |
| 2022/0126117 A1* | 4/2022 | Voronenko | A61N 5/1045 |
| 2022/0230319 A1* | 7/2022 | Andersson | G06T 7/0016 |
| 2023/0302297 A1* | 9/2023 | Lachaine | A61N 5/1039 |

FOREIGN PATENT DOCUMENTS

| | | | | |
|---|---|---|---|---|
| CN | 112263788 A | | 1/2021 | |
| CN | 112546461 A | * | 3/2021 | A61N 5/103 |
| CN | 112755407 A | | 5/2021 | |
| CN | 114225236 A | | 3/2022 | |
| CN | 114529498 A | | 5/2022 | |
| JP | 2020130790 A | | 8/2020 | |
| WO | WO-2018153473 A1 | * | 8/2018 | A61B 5/7292 |

OTHER PUBLICATIONS

Fu, Xiugen et al., Preliminary Application of Optical Surface Monitoring System in Intensity-modulated Radiotherapy for Thoracic Tumors, Chin J Radiol Med Prot, 39(2): 101-106, 2019.

* cited by examiner

100

400

410 obtaining first surface data of a target object to be treated

420

Obtaining historical anatomical image of the target object

430

Determining whether an anatomical image of the target object needs to be reshot for the treatment fraction based on the historical anatomical image and the first surface data

600

700

METHODS AND SYSTEMS FOR RADIATION THERAPY GUIDANCE

CROSS-REFERENCE TO RELATED APPLICATIONS

This application claims priority to Chinese Patent Application No. 202210642270.7, filed on Jun. 8, 2022, the contents of which are incorporated herein by reference.

TECHNICAL FIELD

The present disclosure relates to the field of radiation therapy, and in particular, to systems and methods for radiation therapy guidance.

BACKGROUND

Radiation therapy is widely used in the treatment of cancer or other diseases. Generally, during a treatment planning stage before the treatment starts, a patient may be scanned to acquire an anatomical image with high-definition (e.g., a computed tomography (CT) image), and a radiation therapy plan may be generated based on the anatomical image. According to the radiation therapy plan, the treatment may be delivered to the patient during several treatment fractions, spread over a treatment period of multiple days. During the whole treatment period, the anatomy of the tumor or other tissues (e.g., tissue surrounding the tumor) may change. For example, the tumor may grow, deform, or shrink. After receiving a long term of radiation treatment, habitus and epidermis of the patient may also change. Therefore, the condition of the patient when he/she receives the treatment fraction may be different from that in the treatment planning stage. If the radiation therapy is delivered to the patient according to the initial anatomical image and the radiation therapy plan, the radiation may not be delivered to the target accurately and cause damage to peripheral organs or tissues of the target.

Therefore, it is desirable to provide methods and systems for radiation therapy guidance used to determine whether an anatomical image needs to be reshot for a treatment fraction.

SUMMARY

According to a first aspect of the present disclosure, a method for radiation therapy guidance is provided. The method may be implemented on at least one processor. The method may include obtain first surface data of a target object to be treated by using an optical camera, wherein the first surface data reflects the body surface condition of the target object before a treatment fraction; obtain a historical anatomical image of the target object; determine whether an anatomical image of the target object needs to be reshot for the treatment fraction based on the historical anatomical image and the first surface data.

According to a second aspect of the present disclosure, a system for radiation therapy guidance is provided. The system may include at least one storage device including a set of instructions, and at least one processor configured to communicate with the at least one storage device. When executing the set of instructions the at least one processor is configured to cause the system to perform one or more of the following operations. The system may obtain first surface data of a target object to be treated by using an optical camera. The first surface data reflects the body surface condition of the target object before a treatment fraction. The system may obtain a historical anatomical image of the target object. The system may determine whether an anatomical image of the target object needs to be reshot for the treatment fraction based on the historical anatomical image and the first surface data.

According to a third aspect of the present disclosure, a non-transitory computer-readable medium storing at least one set of instructions is provided. When executed by at least one processor, the at least one set of instructions may cause the at least one processor to implement a method. The method may include obtain first surface data of a target object to be treated by using an optical camera, wherein the first surface data reflects the body surface condition of the target object before a treatment fraction; obtain a historical anatomical image of the target object; determine whether an anatomical image of the target object needs to be reshot for the treatment fraction based on the historical anatomical image and the first surface data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further illustrated in terms of exemplary embodiments, and these exemplary embodiments are described in detail with reference to the drawings. These embodiments are not restrictive. In these embodiments, the same number indicates the same structure, wherein.

DETAILED DESCRIPTION

Figure 1:
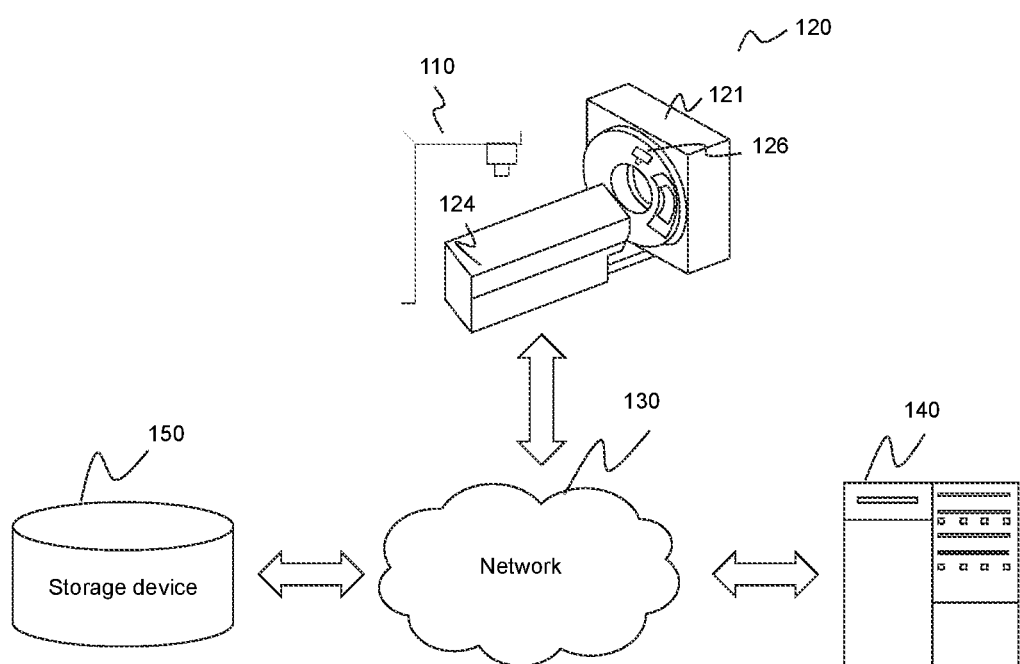
FIG. 1 is a schematic diagram illustrating an exemplary radiation therapy guidance according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

flowcharts are used in the present disclosure to illustrate the operation performed by the system according to the embodiment of the present disclosure. It should be understood that the preceding or subsequent operations are not necessarily performed accurately in sequence. Instead, the steps may be processed in reverse order or simultaneously. At the same time, other operations may add to these procedures, or remove one or more operations from these procedures.

The term "image" in the present disclosure may refer to image data (e.g., scanning data, projection data) and/or images in various forms, including two-dimensional (2D) images, three-dimensional (3D) images, four-dimensional (4D) images, etc. The term "pixel" and "voxel" in the present disclosure may be used interchangeably to refer to elements of an image. The term "anatomical structure" in the present disclosure may refer to gas (e.g., air), liquid (e.g., water), solid (e.g., stone), cell, tissue, organ of a target object, or any combination thereof, which may be displayed in the image (e.g., a historical anatomical image, a computed tomography (CT) image, etc.) and exist in or on human body of the target object. The terms "region" and "position" in the present disclosure may refer to a position of the anatomical structure shown in the image or an actual position of the anatomical structure existing in or on the human body of the target object since the image may indicate the actual position of the anatomical structure existing in or on the human body of the target object. The terms "organ" and "tissue" may be used interchangeably to refer to a portion of the target object.

The present disclosure provides systems and methods for non-invasive imaging and/or treatment, such as disease diagnosis, treatment, or research. In some embodiments, the systems may include a conformal radiation therapy device, an image guided radiation therapy (IGRT) device, an intensity modulated radiation therapy (IMRT) device, an intensity modulated arc therapy (IMAT) device, an emit guidance radiation therapy (EGRT) device, etc., or any combination thereof.

Usually, during a treatment planning stage before the treatment starts, a patient may be scanned to acquire an anatomical image with high-definition (e.g., a computed tomography (CT) image), and a radiation therapy plan may be generated based on the anatomical image. The anatomical image obtained in the treatment planning stage may also be referred to as a planning image. For example, the planning image may be captured during or before the radiation therapy (e.g., on the day of the treatment or a few hours before the treatment) to guide the radiation therapy. According to the treatment plan, the treatment may be delivered to the patient during several treatment fractions, spread over a treatment period of multiple days. During the whole treatment period, the anatomy of the target (e.g., the tumor) or other tissues (e.g., tissue surrounding the tumor) may change. For example, the tumor may grow, deform, or shrink. After receiving a long term of radiation treatment, habitus and epidermis of the patient may also change. Therefore, the condition of the patient when he/she receives the treatment fraction may be different from that in the treatment planning stage. If the radiation therapy is delivered to the patient according to the initial anatomical image and the radiation therapy plan, the radiation may not be delivered to the target accurately and cause damage to peripheral organs or tissues of the target.

The present disclosure provides systems and methods for radiation therapy guidance. Before a treatment fraction is delivered to a target object, surface data that reflects the body surface condition of the target object may be obtained by an optical camera. Whether the current condition of the target object is significantly different from the condition of the target object before the radiation treatment (e.g., in the treatment planning stage) may be determined according to the surface data and a planning image or other historical anatomical image, so as to determine whether an anatomical image needs to be reshot for replanning and ensure that accurate radiation therapy is delivered to the target object.

FIG. 1 is a schematic diagram illustrating an exemplary radiation therapy guidance system 100 according to some embodiments of the present disclosure. As shown in FIG. 1, the radiation therapy guidance system 100 (referred to as the system 100 for brevity) may include an optical camera 110, a radiation therapy device 120, a network 130, a processing device 140, and a storage device 150. In some embodiments, two or more components of the system 100 may be connected with each other through wireless connection (e.g., the network 130), wired connection, or any combination for communication. The connection among the components of the system 100 may be changeable. For example, the optical camera 110 may be connected to the processing device 140 directly or through the network 130. As another example, the storage device 150 may be connected to the processing device 140 directly or through the network 130.

The optical camera 110 may be configured to obtain surface data of a target object to be treated. For example, first surface data of the target object may be obtained using the optical camera 100 before a treatment fraction, and the first surface data may reflect the body surface condition of the target object before the treatment fraction. In some embodiments, a plurality groups of third surface data of the target object may be obtained by using the optical camera 110 before each historical treatment fraction of a plurality of historical treatment fractions, wherein each group of third surface data may reflect the body surface condition of the target object before one of the plurality of historical treatment fractions.

As used herein, surface data of the target object may include any data that can indicate a position, shape, and/or other features of the body surface of the target object. For example, the surface data of the target object may include a three-dimension (3D) image or data set (e.g., 3D space information) of the body surface of the target object. In some embodiments, the optical camera 110 may include a 3D camera configured to obtain a 3D image of the body surface of the target object. Exemplary optical cameras 110 may include a structured light camera, a depth camera, a laser camera, a laser radar, a point cloud camera, etc.

In some embodiments, the optical camera 110 may obtain surface data of the target object to be treated using structured light. In some embodiments, the optical camera 110 may include one or more groups of binocular cameras. More descriptions of the optical camera 110 may be found elsewhere in the present disclosure, e.g., FIG. 2 and relevant descriptions, which is not repeated here.

The radiation therapy device 120 may be configured to deliver radiation therapy on the target object. For example, the radiation therapy device 120 may alleviate symptoms of the target object by delivering one or more radiation beams to treatment regions (e.g., a tumor) of the target object. The radiation beam may include a plurality of radiation beamlets. In the present disclosure, the target object may include any biological target objects (e.g., human bodies, animals, plants, or a portion thereof) and/or non-biological target objects (e.g., phantoms). For example, the target object may include an actual portion of the human body, such as the head, the chest, the abdomen, or any combination thereof. In some embodiments, the radiation therapy device 120 may be a conformal radiation therapy device, an image guidance radiation therapy (IGRT) device, an intensity modulated radiation therapy (IMRT) device, an intensity modulated arc therapy (IMAT) device, an emit guidance radiation therapy (EGRT) device, etc.

In some embodiments, the radiation therapy device 120 may include a body frame 121, a treatment component 126, a treatment bed 124, etc. The treatment component 126 may include a treatment radiation source, an accelerator, etc. The body frame 121 may be configured to install the treatment component 126. The target object may be placed on the treatment bed 124 to receive the radiation therapy and/or scanning. The treatment component 126 may emit radiation rays for treatment toward the target object. The radiation rays may be in the form of particles, which may be accelerated by components (such as an accelerator) and radiate on the target object. The radiation rays may include photon, electron, proton, neutron, or the like, or any combination thereof.

In some embodiments, the radiation therapy device 120 may further include an imaging component. The imaging component may generate an anatomical image of the target object before, during, or after a treatment. The imaging component may include a computed tomography (CT) component, an ultrasonic imaging component, a fluoroscopy imaging assembly, a magnetic resonance imaging (MRI) component, or any combination thereof. The imaging component and the treatment component 126 may share a same body frame or different body frames. In some embodiments, the imaging component may be configured to obtain a historical anatomical image of the target object.

The network 130 may include any suitable network for exchanging information and/or data of the system 100. In some embodiments, one or more components of the system 100 (e.g., the optical camera 110, the radiation therapy device 120, the processing device 140, the storage device 150, etc.) may communicate data and/or information with one or more components of the system 100 via the network 130. For example, the processing device 140 may obtain image data from the radiation therapy device 120 via the network 130. As another example, the processing device 140 may obtain surface data of the target object from the optical camera 110 via the network 130.

The network may be a public network (e.g., Internet), a private network (e.g., a local area network (LAN), a wide area network (WAN)), a wired network (e.g., Ethernet), a wireless network (e.g., 802.11 network, WiFi network), a cellular network (e.g., a long-term evolution (LTE) network), a frame relay network, a virtual private network ("VPN"), a satellite network, a telephone network, a router, a hub, a switch, a server computer, and/or any combination thereof. Merely for example, the network 130 may include a cable network, a wired network, an optical network, a telecommunication network, an intranet, a wireless local area network (WLAN), a metropolitan area network (MAN), a public switched telephone network (PSTN), a Bluetooth™ network, a purple Bee™ network, a near-field communication (NFC) network, or any combination thereof. In some embodiments, the network 130 may include one or more network access points. For example, the network 130 may include wireless and/or wired network access points such as a base station and/or an internet switching point, and the one or more components of the system 100 may exchange data and/or information by connecting to the network 130 via these access points.

The processing device 140 may process data and/or information obtained from the optical camera 110, the radiation therapy device 120, and/or the storage device 150. In some embodiments, the processing device 140 may be a single sever or server group. The sever groups may be centralized or distributed. In some embodiments, the processing device 140 may be local or remote. For example, the processing device 140 may access information and/or data stored in the optical camera 110, the radiation therapy device 120, and/or the storage device 150 via the network 130 or directly. In some embodiments, the processing device 140 may be implemented on a cloud platform. Merely as an example, the cloud platform may include a private cloud, a public cloud, a hybrid cloud, a community cloud, a distributed cloud, an internal cloud, a multi-layer cloud, or any combination thereof.

The storage device 150 may store data, instructions, and/or any other information. In some embodiments, the storage device 150 may store data obtained from the optical camera 110, the radiation therapy device 120, and/or the processing device 140. In some embodiments, the storage device 150 may store data and/or instructions, and the processing device 140 may execute or use the data and instructions to execute exemplary methods described in the present disclosure. In some embodiments, the storage device 150 may include a mass memory, a removable memory, a volatile read-write memory, a read-only memory (ROM), or any combination thereof. In some embodiments, the storage device 150 may be executed on a cloud platform. Merely as an example, the cloud platform may include a private cloud, a public cloud, a hybrid cloud, a community cloud, a distributed cloud, an internal cloud, a multi-layer cloud, etc. or any combination thereof.

In some embodiments, the storage device 150 may communicate with one or more other components (e.g., the processing device 140, the optical camera 110, and the radiation therapy device 120) of the system 100 via the network 130 or directly. The one or more components of the system 100 may access data or instructions stored in the storage device 150 via the network 130. In some embodiments, the storage device 150 may be part of the processing device 140.

Figure 2:
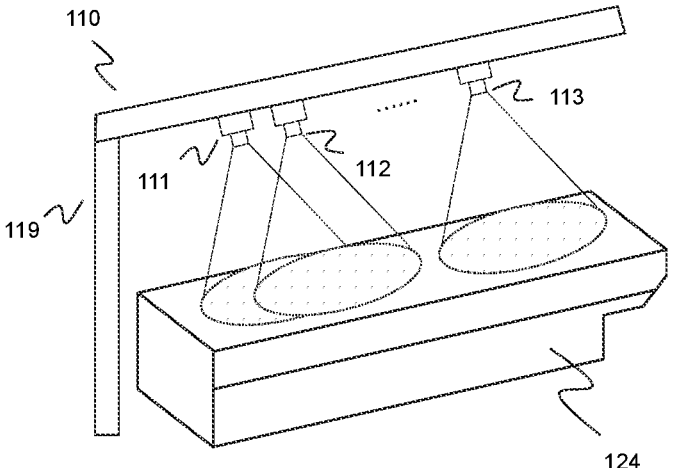
FIG. 2 is a schematic diagram illustrating an exemplary optical camera according to some embodiments of the present disclosure.

FIG. 2 is a schematic diagram illustrating an exemplary optical camera according to some embodiments of the present disclosure. As shown in FIG. 2, the optical camera may be placed near a treatment bed 124 and configured to obtain surface data of a target object (not shown in FIG. 2) placed on the treatment bed 124. The optical camera 110 may include a camera support 119 and a plurality of cameras (e.g., a camera 111, a camera 112, . . . , a camera 113). Each camera may be configured to obtain surface data of a portion of the target object. In some embodiments, a count of cameras may be adjusted according to the actual condition, for example, the count of cameras may be two, three, four, five, etc. The structures of different cameras may be the same or different. The plurality of cameras may be placed on the camera support 119 with equal or unequal intervals.

In some embodiments, a camera in the optical camera 110 may be a binocular camera. Each binocular camera may include a projector and two detectors. The two detectors may be located at different positions beside the target object to achieve high-precision three-dimension positioning. The projector may project a certain mode of structured light (e.g., an infrared light) onto surface of the target object, the structure light reflected by the surface of the target object may be received by the detectors to obtain 3D spatial information and generate a 3D image. The structured light emitted by the projector may include a stripe structured light, a point structured light, a checkerboard structured light, or any other forms of structured light. In some embodiments, the camera of the optical camera 110 may merely include one projector and one detector.

In some embodiments, each binocular camera may obtain surface data (e.g., a 3D image) of a portion of the target object within its field of view (FOV). The surface data captured by the plurality of binocular cameras may be fused to generate surface data of the whole target object. In some embodiments, by setting the positions of binocular cameras, a combination of the FOVs of all the binocular cameras may cover the whole human body portion of the target object. In some embodiments, in order to obtain complete surface data of the target object (i.e., surface data of the whole target object), the FOVs of adjacent binocular cameras may partially be overlapped. The surface data of the portions of the target object captured by the plurality of binocular cameras may be fused (e.g., stitched) according to the overlapped regions to generate the complete surface data of the target object.

In some embodiments, a spatial position of the body surface of the target object may be observed quickly with high accuracy (e.g., the body surface features near a tumor of a patient can be observed with submillimeter accuracy) by an optical detection method (e.g., using the optical camera 110), which can be used to accurately evaluate the physical condition of the target object before the treatment fraction, so as to compare with the physical condition of the target object when a historical anatomical image is captured, and further determine whether an anatomical image needs to be reshoot for replanning.

It should be noted that the above the system 100 and the optical camera 110 are provided for illustrative purposes only and not intended to limit the scope of the present disclosure. For those skilled in the art, many changes and modifications can be made under the guidance of the content of the present disclosure. For example, the optical camera 110 may include a plurality of camera supports and a plurality of binocular cameras, and each binocular camera may be installed on one camera support.

Figure 3:
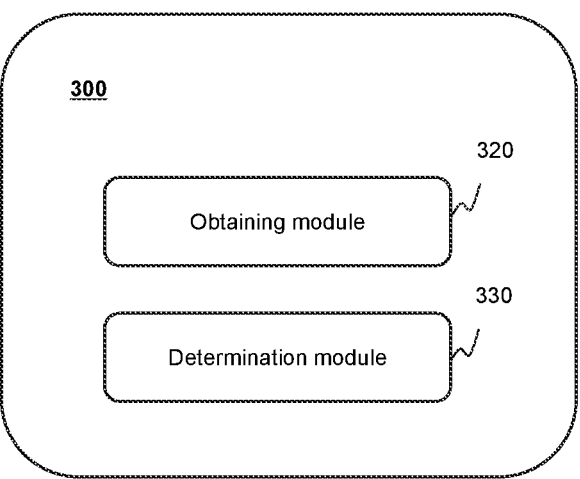
FIG. 3 is a block diagram illustrating an exemplary processing device according to some embodiments of the present disclosure.

FIG. 3 is a block diagram illustrating an exemplary processing device 140 according to some embodiments of the present disclosure. As shown in FIG. 3, the processing device 140 may include an obtaining module 310 and a determination module 320.

The obtaining module 310 may be configured to obtain surface data of the target object (or a portion thereof) captured by the optical camera and a historical anatomical image of the target object. In some embodiments, the obtaining module 310 may obtain the surface data of a portion of the target object captured by each binocular camera and stitch the surface data to generate complete surface data of the target object. In some embodiments, the obtaining module 310 may obtain first surface data of the target object to be treated, wherein the first surface data may reflect the body surface condition of the target object before a treatment fraction. In some embodiments, the obtaining module 310 may obtain a plurality groups of third surface data corresponding to a plurality of historical treatment fractions, each group of third surface data may reflect the body surface condition of the target object before one of the plurality of historical treatment fractions.

In some embodiments, the obtaining module 310 may obtain a deformation model relating to a physiological motion of the target object. In some embodiments, the obtaining module 310 may further obtain feature information of the target object and a trained judgment model. In some embodiments, the obtaining module 310 may further obtain initial surface data of the target object captured by the optical camera and obtain a target reference model from a reference database. More descriptions of the obtaining module 310 may be found elsewhere in the present disclosure (e.g., relevant descriptions of operations 410 and 420).

The determination module 320 may be configured to determine whether an anatomical image of the target object needs to be reshot for the treatment fraction based on the historical anatomical image and the first surface data. In some embodiments, the determination module 320 may determine second surface data of the target object based on the historical anatomical image, wherein the second surface data may reflect the body surface condition of the target object when the historical anatomical image is captured. In some embodiments, the determination module 320 may generate a first comparison result by comparing the first surface data with the second surface data, and determine whether an anatomical image of the target object needs to be reshot for the treatment fraction based on the first comparison result. In some embodiments, the determination module 320 may obtain a corrected comparison result by correcting the first comparison result based on the deformation model, and determine whether an anatomical image of the target object needs to be reshot for the treatment fraction based on the corrected comparison result. In some embodiments, the determination module 320 may determine whether an anatomical image of the target object needs to be reshot for the treatment fraction by processing the feature information of the target object, the historical anatomical image, and the first surface data using the trained judgment model. In some embodiments, the determination module 320 may generate a plurality of third comparison results by comparing each group of third surface data with the second surface data, wherein whether an anatomical image of the target object needs to be reshot for the treatment fraction may be further determined based on the plurality of third comparison results. In some embodiments, in response to determining that the anatomical image of the target object does not need to be reshot for the treatment fraction, the determination module 320 may designate a radiation therapy plan corresponding to the historical anatomical image as a radiation therapy plan to be delivered for the treatment fraction. In some embodiments, in response to determining that an anatomical image of the target object needs to be reshot for the treatment fraction, the determination module 320 may re-generate a radiation therapy plan for the treatment fraction based on the reshot anatomical image of the target object.

More descriptions of determining whether an anatomical image of the target object needs to be reshot for the treatment fraction based on the historical anatomical image and the first surface data may be found elsewhere in the present disclosure (e.g., relevant descriptions of operation 430).

It should be noted that the above description of the processing device 140 and its modules is only for the convenience of description and does not limit this specification to the scope of the embodiments. It can be understood that for those skilled in the art, after understanding the principle of the system, they may combine the modules arbitrarily, or form a subsystem to connect with other modules without departing from this principle. For example, the obtaining module 310 and the determination module 320 in FIG. 3 may be different modules in a system or integrated into a single module to implement functions of two modules. As another example, the modules may share a same storage module, or each of the modules may include its respective storage module. Such deformations are within the scope of protection of the present disclosure.

In some embodiments, the processing device may further include a training module configured to generate one or more machine learning models disclosed herein. In some embodiments, the training module and other modules described above may be implemented on different computing devices. Merely by way of example, the training module may be implemented on a computing device of a vendor of the machine learning model(s), while the other modules described above may be implemented on a computing device of a user of the machine learning model(s).

Figure 4:
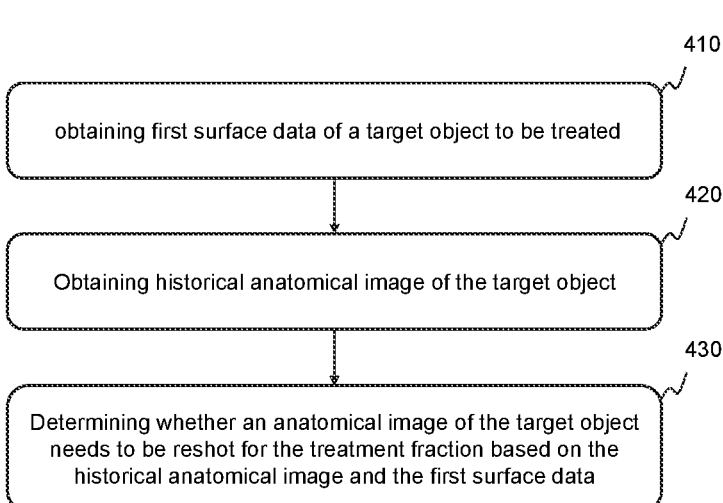
FIG. 4 is a flowchart illustrating an exemplary process for radiation therapy guidance according to some embodiments of the present disclosure.

FIG. 4 is a flowchart illustrating an exemplary process for radiation therapy guidance according to some embodiments of the present disclosure.

As described elsewhere in the present disclosure, during a treatment planning stage before the treatment starts, a patient may be scanned to acquire an anatomical image with high-definition (e.g., a computed tomography (CT) image), and a radiation therapy plan may be generated based on the anatomical image. The treatment may be delivered to the patient during several treatment fractions, spread over a treatment period of multiple days. During the whole treatment period, the anatomy of the target (e.g., the tumor) or other tissues (e.g., tissue surrounding the tumor) may change. For example, the tumor may grow, deform, or shrink. Therefore, the condition of the patient when he/she receives the treatment fraction may be different from that in the treatment planning stage. If the radiation therapy is delivered to the patient according to the initial anatomical image and the radiation therapy plan, the radiation may not be delivered to the target accurately and cause damage to peripheral organs or tissues of the target. Therefore, it is desirable to provide a radiation therapy guidance method used to determine whether an anatomical image needs to be reshot for the treatment fraction.

In some embodiments, the process 400 may be executed during a radiation treatment that is delivered to a target object via a plurality of radiation fractions. In some embodiments, if the radiation therapy may be divided into N treatment fractions, the process 400 may be executed before any treatment fraction (e.g., a second treatment fraction, a third treatment fraction, a fifth treatment fraction, etc.) to verify whether an anatomical image and/or the treatment plan need to be updated for the treatment fraction. For example, when the patient has received three treatment fractions and is about to receive a fourth treatment fraction, since it is possible that the condition of the patient has a relatively big difference compared with the condition of the patient when an anatomical image corresponding to the radiation therapy plan is captured, the process 400 may be executed to verify whether an anatomical image and/or the radiation therapy plan need to be updated for the fourth treatment fraction.

In 410, first surface data of a target object to be treated may be obtained. In some embodiments, the process 410 may be executed by the obtaining module 310 and/or the determination module 320 of the processing device 140.

The target object to be treated may be an object that needs to receive the radiation therapy, such as a cancer patient. The first surface data may reflect the body surface condition of the target object before a treatment fraction, such as position and shape features of each portion of the body surface of the target object. In some embodiments, the first surface data may include a 3D image or data set (e.g., 3D spatial information of points on the body surface of the target object) corresponding to the target object. For example, the first surface data may be point cloud data, depth data, etc.

In some embodiments, the process 400 may be executed before the treatment fraction, such as several hours or several minutes before the treatment fraction. The first surface data may reflect the body surface condition of the target object before the treatment fraction. The first surface data of the target object may compare with historical data of the target object to determine whether the target object has a relatively big change.

In some embodiments, the first surface data of the target object may be acquired by an optical detection method. The optical detection method may be used to detect and reconstruct a body surface structure of the target object by emitting and receiving rays (e.g., infrared rays). In some embodiments, the obtaining module 310 may obtain the first surface data of the target object to be treated by using an optical camera (e.g., the optical camera 110). The first surface data may include original data (e.g., an optical image, point cloud data) collected by the optical camera and/or data generated based on the original data. The surface data may be generated by the optical camera directly or the obtaining module 310. In some embodiments, the optical camera may include a binocular camera. In some embodiments, the optical camera may include a plurality of binocular cameras. Each binocular camera may collect surface data of the target object within its FOV. In order to obtain whole surface data of the target object, the FOVs of the binocular cameras may cover the whole human body portion of the target object. More descriptions of the optical camera and a binocular camera may be found elsewhere in the present disclosure (e.g., relevant descriptions of FIG. 1 and FIG. 2).

In some embodiments, the obtaining module 310 may obtain surface data of a portion of the target object collected by each binocular camera, the determination module 320 may determine the first surface data of the target object based on the surface data of the portion of the target object collected by each binocular camera. For example, the FOVs of adjacent binocular cameras may be partially overlapped, the determination module 320 may generate complete surface data of the target object according to the overlapped regions in the groups of surface data collected by the binocular cameras.

In some embodiments, the surface data of a portion of the target object captured by a binocular camera may include a partial image that reflects the body surface condition of the portion of the target object within the FOV of the binocular camera. The complete surface data may include a whole-body image that reflects the surface body condition of the whole body of the target object. In some embodiments, the determination module 320 may generate a whole-body image by stitching a plurality of partial images according to the overlapped regions in the plurality of partial images of the target object. The overlapped regions in adjacent partial images correspond to a same portion of the target object, so that image stitching can be performed based on the overlapped regions. In some embodiments, the determination module 320 may determine the first surface data of the target object according to the whole-body image of the target object. For example, the determination module 320 may designate 3D spatial information corresponding to the whole-body of the target object extracted from the whole-body image as the first surface data.

In some conditions, since a distance between the target object and the optical camera is relatively far, the initial surface data (e.g., point cloud data) collected by the optical camera is sparse and can not reflect the body surface condition of the target object in detail, and subsequent comparison with second surface data and/or third surface data may have a relatively low accuracy. Therefore, the initial surface data captured by the optical camera may need to be corrected to generate surface data including denser points.

For example, the obtaining module 210 may obtain the initial surface data of the target object captured by the optical camera. The obtaining module 210 may also obtain a target reference model from a reference database based on feature information of the target object. The feature information of the target object may include information that reflects the body condition of the target object. Exemplary feature information of the target object may include information such as the tumor type, a body shape (e.g., height, fatness, etc.), age, gender, etc., of the target object. The reference database may store a plurality of reference models of different types of objects. A reference model of a specific type of object may include detail body surface data of this specific type of object. For example, patients may be divided into different types according to features, such as age, gender, shape, tumor types, etc., and a reference model corresponding to each type of patients may be generated. Merely for example, the reference database may store sets of detail point cloud data corresponding to men and women in multiple age groups (e.g., 1-10, 11-20, and 21-30). Detail point cloud data of a specific type of patient may be simulated and generated according to standard anatomical features of the specific type of patients, or collected using a plurality of optical cameras near patients of this specific type.

In some embodiments, the processing device 140 or other computer devices may generate the reference models of the plurality types of objects and store the reference models in the reference database. The reference database may be the storage device 150 or other storage devices. The obtaining module 210 may obtain the reference model corresponding the type of the target object from the storage device 150 as the target reference model. For example, the gender and the age group of the target object may be determined according to the feature information of the target object, and a reference model corresponding to the gender and the age group of the target object may be regarded as the target reference model.

After the target reference model is obtained, the determination module 220 may determine the first surface data by correcting the initial surface data based on the target reference model. For example, the determination module 220 may predict surface points of the target object based on the target reference model and add these predicted surface points into the initial surface data to determine the first surface data. Optionally, the points in the target reference model may be designated as the predict surface point directly, or the points in the target reference model may be adjusted based on the feature information of the target object and designated as the predict surface points. The corrected initial surface data can reflect detail information of the body surface condition of the target object better compared with the initial surface data before the correction, thereby generating an analysis result based on the first surface data having an improved accuracy.

Traditional radiation therapy guidance approaches (e.g., IGRT) usually collect a guidance image before a treatment fraction, and compare the guidance image with a historical anatomical image. Since the guidance image has a relatively low resolution, the accuracy of these guidance approaches is low. according to some embodiments of the present disclosure, body surface features of the target object may be captured using optical detection methods with high accuracy. In addition, the optical detection methods can detect the body surface features of the target object fast without bringing additional radiation to the target object, which reduces the radiation damage to the target object, and has a relatively high security and applicability.

In 420, a historical anatomical image of the target object may be obtained. In some embodiments, the operation 420 may be executed by the obtaining module 310 of the processing device 140.

The historical anatomical image may reflect an internal structure of the target object. For example, the historical anatomical image may be used to identify one or more diseased organs and/or peripheral organs thereof. In some embodiments, the historical anatomical image may be an anatomical image including the whole-body of the target object. Alternatively, the historical anatomical image may be an anatomical image including a portion of the target object, such as a diseased organ and its peripheral organs of the target object. In some embodiments, the historical anatomical image may be one or more of a CT image, an MRI image, an electronic portal imaging device (EPID) image, etc. The historical anatomical image may include a 2D image or a 3D image.

In some embodiments, the historical anatomical may be a planning image captured before the radiation treatment or an anatomical image captured during a historical treatment fraction that has been performed. For example, if the treatment fraction to be performed is the third treatment fraction, the historical anatomical image may be an anatomical image captured in a first treatment fraction or a second treatment fraction.

In some embodiments, the obtaining module 310 may obtain the historical anatomical image from the radiation therapy device (e.g., the radiation therapy device 120) or the storage device 150.

In 430, whether an anatomical image of the target object needs to be reshot for the treatment fraction may be determined based on the historical anatomical image and the first surface data. In some embodiments, the operation 430 may be executed by the determination module 320 of the processing device 140.

The historical anatomical image may be used to determine the body surface condition of the target object when the historical anatomical image is captured, which may be compared with the first surface data obtained before the current treatment fraction, and whether an anatomical image of the target object needs to be reshot for the current treatment fraction may be determined based on the comparison result. In some embodiments, the determination module 320 may determine second surface data of the target object based on the historical anatomical image, the second surface data may reflect the body surface condition of the target object when the historical anatomical image is captured. For example, the second surface data may reflect a body surface swelling degree, an internal quality distribution status, and an overall fat mass distribution of a region of interest (e.g., a diseased region to be treated). The second surface data may also reflect the body surface, and in particular, a skin texture state of the body surface in the region of interest.

Further, the determination module 320 may generate a first comparison result by comparing the first surface data with the second surface data, and determine whether an anatomical image of the target object needs to be reshot for the treatment fraction based on the first comparison result. The first comparison result may reflect a difference between the body surface condition of the target object when the historical anatomical image is captured and the body surface condition of the target object before the treatment fraction. For example, the first comparison result may be a difference value or similarity degree between the first surface data and the second surface data. For example, the first surface data and the second surface data may be 3D images displaying a surface shape of the target object, the first comparison result may be a similarity degree between the two 3D images that is within a range of 0-1, the closer the value is to 1, the more similar the two 3D images are. As another example, the first surface data may include a first 3D coordinate of each point on the body surface of the target object, the second surface data may include a second 3D coordinate of each point on the body surface of the target object, and the first comparison result may include a difference value between the first and second 3D coordinates of each point.

In some embodiments, a similarity degree between the first surface data and the second surface may be determined based on similarity algorithms, such as a structural similarity index (SSIM) algorithm, a Histogram-based similarity algorithm, a hash algorithm, a cosine similarity algorithm, a Jaccard similarity algorithm, etc. In some embodiments, the determination module 320 may determine first value(s) of one or more surface feature parameters based on the first surface data and determine second value(s) of the one or more surface feature parameters based on the second surface data. Exemplary surface feature parameters may include the surface area, lengths in different directions (e.g., an axial direction, a radial direction, etc.), positions of one or more feature points (e.g., a critical point), etc., of the target object. The determination module 320 may further determine the first comparison result by comparing the first value(s) with the second value. Merely for example, the first comparison result may include a difference value between the first value and the second value of a surface feature parameter.

In some embodiments, the determination module 320 may eliminate the effect of positioning difference of the target object by registering the first surface data and the second surface data. Further, the determination module 320 may generate a first comparison result by performing a first comparison between the registered first surface data and the registered second surface data. In some embodiments, the determination module 320 may generate a first comparison result by performing whole-body registration and local registration on the first surface data and the second surface data. More descriptions of registering the first surface data and the second surface data may be found in relevant descriptions of FIG. 5, which is not repeated herein.

In some embodiments, the determination module 320 may determine whether an anatomical image of the target object needs to be reshot for the treatment fraction based on the first comparison result and a comparison threshold. For example, if the first comparison result is greater than the comparison threshold, the difference value between the first surface data and the second surface data may be relatively big, changes in the body of the target object may exceed an acceptable range and an anatomical image of the target object needs to be reshot; if the first comparison result is less than the comparison threshold, the difference value between the first surface data and the second surface data may be relatively small, the changes in the body of the target object may do not exceed the acceptable range and an anatomical image of the target object does not need to be reshot.

In some embodiments, the comparison threshold may be a system default value or set manually. Alternatively, the comparison threshold may be determined by the determination module 320 through data analysis. In some embodiments, the comparison threshold may be determined based on relevant information of a region of interest of the target object. The region of interest may include a diseased region (e.g., a tumor) to be treated and/or one or more peripheral organs. In some embodiments, the relevant information of the region of interest may include information, such as the size, the position, the treatment condition, the organ type, the importance, etc., of the diseased region and/or the peripheral organs. Merely for example, when an important organ of the patient is near the diseased region, in order to avoid damage to the nearby organ, the comparison threshold may be set to be relatively low, and an acceptable difference value between the first surface data and the second surface data may be relatively small. In some embodiments, the determination module 320 may determine the comparison threshold based on the feature information of the target object such as age, gender, etc., of the patient. In some embodiments, the determination of the comparison threshold may consider various conditions comprehensively rather than using a fixed value. Since the acceptable changes in the body condition of the target object in different treatment scenarios (e.g., different sizes of tumor, different positions of tumor) are different, the comparison threshold may be determined according to the actual condition of the target object to improve the accuracy and safety of the treatment.

In some embodiments, the comparison threshold may be determined according to historical samples accumulated in historical diagnosis. Specifically, during a process of historical diagnosis with respect to a patient, if an anatomical image needs to be reshot according to the first surface data and the second surface data of the patient, a new anatomical image may be collected by rescanning the patient. Whether an anatomical image needs to be reshot actually may be determined by tracking the change of an internal structure of the patient according to the new anatomical image and the historical anatomical image captured during the planning stage. Whether the patient is a positive sample object or a negative sample object may be determined according to the determination result. If it is determined that an anatomical image of the patient indeed needs to be reshot based on the newly collected anatomical image (i.e., the determination result based on the newly collected anatomical image is consistent with that based on the first surface data), the patient may be regarded as a positive sample object corresponding to a positive sample. For example, the positive sample may include first surface data (or also be referred to as first sample surface data) and second surface data (or also be referred to as second sample surface data) of the positive sample object, or a difference value between the first surface data and the second surface data. If it is determined that an anatomical image of the patient does not need to be reshot based on the newly collected anatomical image (i.e., the determination result based on the newly collected anatomical image is not consistent with that based on the first surface data), the patient may be regarded as a negative sample object corresponding to a negative sample. For example, the negative sample may include first surface data (or also be referred to as first sample surface data) and second surface data (or also be referred to as second sample surface data) of the negative sample object, or a difference value between the first surface data and the second surface data.

In some embodiments, the processing device 140 or another computer device may generate a second judgment model using the positive and negative samples. The second judgment model may determine whether a sample is a positive sample or a negative sample (i.e., determine whether an anatomical image needs to be reshot for a sample object corresponding to the sample) based on the first sample surface data and the second sample surface of the sample input into the second judgment model. For example, the second judgment model may be a classified model. The processing device 140 may further determine the comparison threshold based on the second judgment model. In some embodiments, the second judgment model may be a machine learning model, e.g., a deep learning model.

In some embodiments, the determination module 320 may predict current internal structure data of the target object based on the first surface data, determine historical internal structure data of the target object based on the historical anatomical image, generate a second comparison result by performing a second comparison between the current internal structure and the historical internal structure data, and determine whether an anatomical image of the target object needs to be reshot for the treatment fraction based on the second comparison result. In some embodiments, the determination module 320 may obtain a plurality groups of third surface data corresponding to a plurality of historical treatment fractions, each third surface data may reflect the body surface condition of the target object before one historical treatment fraction. The determination module 320 may generate a plurality of third comparison results by performing a third comparison between the second surface data and each group of the plurality of third surface data. The determination module 320 may determine whether an anatomical image of the target object needs to be reshot for the treatment fraction based on the third comparison result. In some embodiments, the determination module 320 may perform two or three of the first comparison, the second comparison, and the third comparison, and determine whether an anatomical image of the target object needs to be reshot for the treatment fraction based on a plurality of comparison results. More descriptions of determining whether an anatomical image of the target object needs to be reshot based on the first comparison result, the second comparison result, and the third comparison result may be found in relevant descriptions of FIG. 6, which is not repeated here.

In some embodiments, the obtaining module 310 may obtain feature information of the target object and a trained judgment model. The determination module 320 may determine whether an anatomical image of the target object needs to be reshot for the treatment fraction by using the trained judgment model to process the feature information of the target object, the historical anatomical image, and the first surface data. More descriptions of determining whether an anatomical image needs to be reshot based on the trained judgment model may be found in relevant descriptions of FIG. 7, which is not repeated here.

When collecting the first surface data and the historical anatomical image, since the target object undergoes physiological motion (e.g., respiratory motion, cardiac motion, etc.), inconsistency of physiological phase may exist between the first surface data and the second surface data, which may affect the determination of whether an anatomical image needs to be reshot. Therefore, the first surface data and the second data may be considered to be preprocessed before the comparison or the first comparison result may be corrected after comparing the first surface data with the second surface data, which may reduce the effect of physiological motion of the target object and improve the accuracy of surface data comparison.

In some embodiments, the physiological motion may include respiratory motion, cardiac motion, nerve reflex, digestive motion, etc. In some embodiments, the physiological motion of the target object may be periodic. The physiological motion may have multiple different phases, thus the first surface data and the second surface in the same phase may be compared to eliminate the effect of the physiological motion. For example, the optical camera may be configured to capture a plurality of first frames of the target object before the treatment fraction, the first surface data may be determined based on a target first frame in the plurality of first frames. The historical anatomical image may include a plurality of second frames, the second surface data may be determined based on a target second frame in the plurality of second frames. The target first frame and the target second frame may correspond to the same physiological motion phase relating to the physiological motion.

Taking the respiratory motion as an example, before the treatment fraction, the optical camera may capture data of a patient repeatedly at a plurality of time points, and a respiratory sensor may be used to detect a respiratory signal of the patient during the acquisition of the optical camera. Based on the respiratory signal, the determination module 320 may determine the plurality of first frames captured in the different respiratory phases by the optical camera. A first frame captured in a respiratory phase may include surface data corresponding to the respiratory phase, which may reflect the body surface condition of the target object in the respiratory phase. The historical anatomical image may be obtained by 4D CT scan lasting for a period, thus the historical anatomical image may be a dynamic image and include second frames (i.e., 3D CT images) corresponding to different respiratory phases. A second frame corresponding a respiratory phase may reflect an internal structure of the target object in the respiratory phase.

In order to improve the accuracy of comparison, a target first frame corresponding to a target respiratory phase may be selected from the plurality of first frames, and the first surface data may be determined based on the target first frame; a target second frame corresponding to the target respiratory phase may be selected from the plurality of second frames, and the second surface data may be determined based on the target second frame. For example, the target respiratory phase may be the end expiratory phase, the end inspiratory phase, or any other respiratory phase. As another example, the target respiratory phase may be a respiratory phase of the latest captured first frame, that is, the respiratory phase corresponding to the current first frame latest captured by the optical camera may be tracked in real time, the second frame corresponding to this respiratory phase may be selected from the historical anatomical image for determining the second surface data. Since the respiratory phase of the target first frame is the same as the respiratory phase of the target second frame, the respiratory phases corresponding to the first surface data and the second surface data determined based on the target first frame and the target second frame may also be the same, the effect caused by the physiological motion of the target object may also be the same. By comparing the first surface data with the second surface data in a same phase, the effect generated by the physiological motion during the surface data comparison process may be eliminated or reduced in a certain degree.

In some embodiments, one or more identifiers may be set on the target object (e.g., on the chest and abdomen) while the plurality of first frames of the target object are captured by the optical camera, and image data of the identifiers and a portion region of the target object near the identifiers may be captured by a recording camera. The image data may be used to determine a respiratory signal of the target object during the acquisition of the first frame. The recording camera may be any camera that can capture images in real time, such as the optical camera used to capture the first frames or another camera. In some embodiments, the recording camera may be set in a position near the chest and abdomen of the target object, and the optical camera may be set at a position far away from the chest and abdomen of the target object. The first surface data of the target object captured by the optical camera and the surface data of the chest and abdomen portion captured by the recording camera may be fused, and the fused surface data may be compared to the second surface data corresponding to the historical anatomical image to improve the accuracy of the comparison. In some embodiments, the surface data of the chest and abdomen portion in the first surface data may be replaced by the surface data captured by the recording camera. It should be noted that for physiological motions other than the respiratory motion, the recording camera may be set at other relevant positions of the target object to record the physiological motion of other portions of the target object, and the obtained surface data of the other portions may be fused with the first surface data for comparison with the second surface data.

In some embodiments, in addition to reducing the effect of the physiological motion by comparing the first surface data and the second surface data in the same physiological motion, the determination module 320 may use other physiological motion correction manners. For example, the determination module 320 may correct the first comparison result after comparing the first surface data with the second surface data, which can reduce the effect of physiological motion. Specifically, the first comparison result may be corrected according to a deformation model relating to the physiological motion.

In some embodiments, the obtaining module 210 may obtain a deformation model relating to the physiological motion. The deformation model may reflect a movement process of the target object or a portion of target object (e.g., a chest and abdomen portion affected by respiratory motion) due to the physiological motion. Specifically, before the treatment fraction (e.g., at the planning stage), reference surface data of the target object within a physiological cycle may be collected to analyze non-rigid deformation of the body of the target object caused by the physiological motion, which can be used to establish the deformation model relating to the physiological motion. In some embodiments, the deformation model may include a deformation field that can reflect the deformation condition of each point of the target object or a portion of target object due the physiological motion during the physiological cycle, i.e., a range of non-rigid motion of each point during the physiological cycle.

The determination module 220 may further obtain a corrected comparison result by correcting the first comparison result based on the deformation model. For example, the first comparison result may reflect an offset of each point of the target object. The determination module 220 may determine a deformation value of each point caused by the physiological motion. The determination module 220 may correct the first comparison result by subtracting the deformation value of each point caused by physiological motion from the first comparison result.

In some embodiments, the determination module 220 may determine whether an anatomical image of the target object needs to be reshot for the treatment fraction based on the corrected comparison result. Since the deformation model can reflect the deformation condition of each point of the body of the target object cause by the physiological motion, correcting the first comparison result based on the deformation model may eliminate the effect of the physiological motion to a certain extent to determine a real deformation of the target object caused by pathological changes, and improve the accuracy of determining whether an anatomical image needs to be reshot.

In some embodiments, if it is determined that an anatomical image of the target object needs to be reshot, the determination module 320 may emit an instruction to the medical imaging device (e.g., a CT device) to rescan the target object or prompt a user to rescan the target object. After an anatomical image is recaptured, the user or the determination module 320 may determine whether a radiation therapy plan needs to updated according to the recaptured anatomical image. In some embodiments, the recaptured anatomical image may be regarded as a historical anatomical image for the next treatment fraction.

In some embodiments, in response to determining that an anatomical image of the target object does not need to be reshot for the treatment fraction, the determination module 320 may set the radiation therapy plan corresponding to the historical anatomical image as a radiation therapy plan to be delivered for the treatment fraction. The radiation therapy plan corresponding to the historical anatomical image may be generated based on the historical anatomical image of the target object, which includes treatment measures applied to be applied on the target object in a plurality of treatment fractions. In some embodiments, the determination module 320 may transmit an instruction and the radiation therapy plan to the radiation therapy device to direct the radiation therapy device to deliver the treatment fraction. Alternatively, the determination module 320 may prompt the user that the target object does not need to be reimaged, and the user may further control the radiation therapy device to perform the radiation therapy on the target object based on the radiation therapy plan.

In some embodiments, in response to determining that an anatomical image of the target object needs to be reshot for the treatment fraction, the determination module 320 may generate a new radiation therapy plan for the treatment fraction based on the recaptured anatomical image of the target object. In some embodiments, the determination module 320 may transmit an instruction and the new radiation therapy plan to the radiation therapy device to direct the radiation therapy device to deliver the treatment fraction. Alternatively, the determination module 320 may prompt the user that the new radiation therapy plan has been generated based on the recaptured anatomical image, and the user may further control the radiation therapy device to perform the radiation therapy on the target object based on the new radiation therapy plan.

In some embodiments, the first surface data with high-accuracy may be obtained by the optical detection method. Based on the first surface data and the historical anatomical image, whether the treatment fraction can be delivered according to the initial anatomical image and the initial treatment plan may be determined, and the user may be prompted to perform a new scan for the target object when necessary to ensure the accuracy of radiation therapy. On the other hand, the optical camera used in the present disclosure may not cause additional radiation damage to the target object and has higher safety.

It should be noted that the above description of process 400 is merely provided for illustration purposes, and does not limit the scope of the present disclosure. For those skilled in the art, various modifications and changes can be made to the process 400 under the guidance of the present disclosure. However, these amendments and changes are still within the scope of the present disclosure. For example, the operations 410 and 420 may be performed synchronously.

Figure 5:
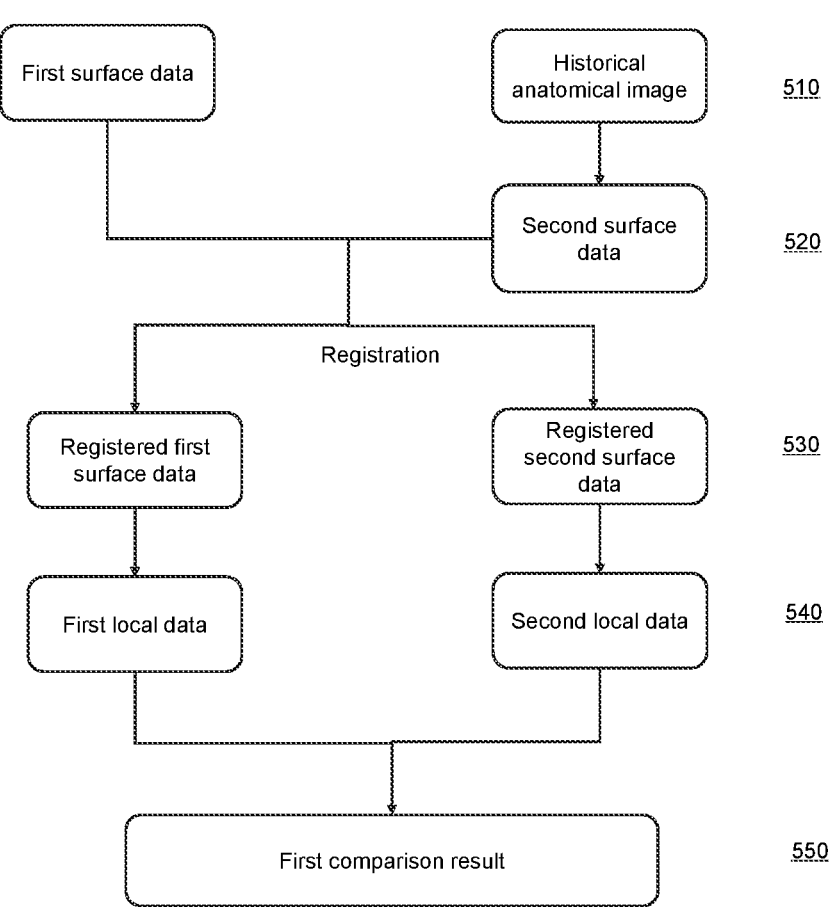
FIG. 5 is a flowchart illustrating an exemplary process for determining a first comparison result according to some embodiments of the present disclosure.

FIG. 5 is a flowchart illustrating an exemplary process for determining a first comparison result according to some embodiments of the present disclosure. In some embodiments, one or more operations of the process 500 may be executed to implement at least part of operation 430 in FIG. 4.

In 510, a historical anatomical image and first surface data of the target object may be obtained. In some embodiments, the operation 510 may be executed by the obtaining module 310 and/or the determination module 320 of the processing device 140. More descriptions of the acquisition of the first surface data and the historical anatomical image may be found in the operations 410 and 420, which is not repeated here.

In 520, second surface data of the target object may be determined based on the historical anatomical image. In some embodiments, the operation 520 may be executed by the determination module 320 of the processing device 140. More descriptions of the determination of the second surface data may be found in the operation 430, which is not repeated here.

In 530, the first surface data and the second surface data may be registered. In some embodiments, the operation 530 may be executed by the determination module 320 of the processing device 140.

As discussed in FIG. 4, the first surface data may reflect the body surface condition of the target object before the treatment fraction, and the second surface data may reflect the body surface condition of the target object when the historical anatomical image is captured. Since the positionings of the target object may be different before the treatment fraction and when the historical anatomical image is captured, the determination module 320 may register the first surface data and the second surface data, which may eliminate and reduce the effect of the positioning difference for the subsequent judgment. The registration refers to a process for matching two or more of images of a same object. During the process of registering the first surface data and the second surface data, data of the first surface data and the second surface data corresponding to the same body portion of the target object may be matched.

In some embodiments, the registering the first surface data and the second surface data may include rigid registration and/or non-rigid registration. In some embodiments, the registration of the first surface data and the second surface data may be performed based on one or more registration algorithms, such as a gray-based matching algorithm, a feature-based matching algorithm, and a domain transformation-based matching algorithm.

In 540, first local data and second local data corresponding to a region of interest of the target object may be determined from the registered first surface data and the registered second surface data, respectively. In some embodiments, the operation 540 may be executed by the determination module 320 of the processing device 140.

The region of interest of the target object may include a diseased portion (e.g., a tumor portion) of the target object. In some embodiments, since other portions near the diseased portion may also change, the region of interest of the target object may further include periphery portions of the diseased portion, such as one or more periphery organs. In some embodiments, the region of interest of the target object may include the stomach, a lung, the head, etc.

In some embodiments, data corresponding to the same body portion in the registered first surface data and the register second surface data has been matched, which can eliminate or reduce the difference of the region of interest of the target object caused by the body positioning or posture, so that the difference between the region of interest of the target object before the treatment fraction and when the historical anatomical image is captured can be determined accurately.

In some embodiments, the determination module 320 may extract first local data and second local corresponding to the region of interest of the target object from the registered first surface data and the registered second surface data, respectively. In some embodiments, the first local data may be surface data corresponding to the region of interest of the target object in the first surface data, which reflects body surface features of the region of interest of the target object before the treatment fraction; the second local data may be surface data corresponding to the region of interest of the target object in the second surface data, which reflects body surface features of the region of interest of the target object when the historical anatomical image is captured. By processing the first local data and the second local data, whether the region of interest of the target object changes may be determined accurately.

In 550, a first comparison result may be generated by comparing the first local data with the second local data. In some embodiments, the operation 550 may be executed by the determination module 320 of the processing device 140.

In some embodiments, the determination module 320 may perform registration between the first local data and the second local data, and obtain a first comparison result by calculating a similarity degree between the registered first local data and the registered second local data. In some embodiments, since the first local data and the second local data correspond to the same region of interest, the whole-body registration result may be optimized by performing local registration, so as to improve the registration accuracy of the region of interest.

In some embodiments, the first comparison result may be a difference value or similarity between the first local data and the second local data. Merely for example, the first local data and the second local data may be a 3D image displaying surface shape of the region of interest of the target object, and the first comparison result may be a similarity value between the two 3D images that is within a range of 0-1, the closer the value is to 1, the more similar the two 3D images are. As another example, the first local data and the second local data may be a 3D coordinate of each point of the body local of the target object, the first comparison result may be a difference value between the 3D coordinates of each point in the first local data and the second local data.

In some embodiments, if merely registering the whole-body data of the target object, it may not be possible to accurately determine the changes of the diseased portion and peripheral portions of the target object; if merely registering the local data of the region of interest of the target object, the conditions of the diseased portion and peripheral portions of the target object may be misjudged due to the different body positionings or different postures of the target object. Therefore, the local data may be registered under the basis of the whole-body registration to obtain an accurate comparison result.

In some embodiments, when comparing the first surface data (or the first local data) with the second surface data (or the second local data), certain methods may be adapted to eliminate the possible effects caused by the physiological motion (e.g., the respiratory motion) of the target object. More descriptions of the manners for eliminating the effects of the physiological motion may be found in the operation 430 and relevant descriptions, which is not repeated here.

It should be noted that the above description of process 500 is merely provided for illustration purposes, and does not limit the scope of the present disclosure. For those skilled in the art, various modifications and changes can be made to the process 500 under the guidance of the present disclosure. However, these amendments and changes are still within the scope of the present disclosure. For example, the operation 530 may be omitted. The determination module 320 may determine the first local data and the second local data in the first surface data and the second surface data directly.

Figure 6:
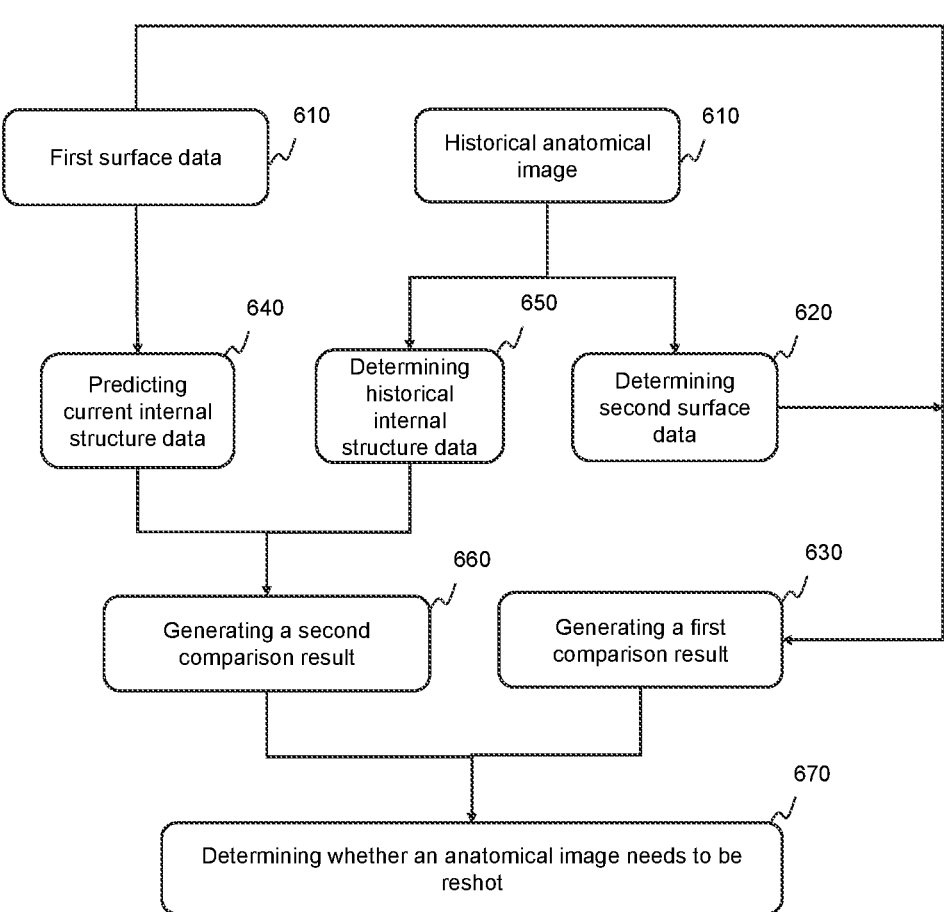
FIG. 6 is a flowchart illustrating an exemplary process for radiation therapy guidance according to some embodiments of the present disclosure.

FIG. 6 is a flowchart illustrating an exemplary process for radiation therapy guidance according to some embodiments of the present disclosure. In some embodiments, the process 600 may be an exemplary embodiment of the process 400 as described in connection with FIG. 4.

In 610, a historical anatomical image and first surface data of the target object may be obtained. In some embodiments, the operation 610 may be executed by the obtaining module 310 and/or the determination module 320. More descriptions of the acquisition of the first surface data and the historical anatomical image may be found in the operations 410 and 420, which is not repeated here.

In 620, second surface data of the target object may be determined based on the historical anatomical image. In some embodiments, the operation 620 may be executed by the determination module 320. More descriptions of determination of the second surface data may be found in the operation 430, which is not repeated here.

In 630, a first comparison result may be generated by performing a first comparison between the first surface data and the second surface data. In some embodiments, the operation 630 may be executed by the determination module 320. More descriptions of the first comparison may be found in relevant descriptions of the operation 430 and FIG. 5, which is not repeated here.

In 640, current internal structure data of the target object may be predicted based on the first surface data. In some embodiments, the operation 640 may be executed by the determination module 320.

The current internal structure data may reflect the internal structure condition of the target object before the treatment fraction. In some embodiments, the internal structure data may include internal structure parameters of the target object, such as the position, the shape, the size, etc., of internal organs. In some embodiments, the internal structure data may include an image that reflects an internal structure of the target object. In some embodiments, the determination module 320 may predict the current structure data based on a model. For example, the determination module 320 may obtain the current internal structure data based on a trained internal structure prediction model.

In some embodiments, the obtaining module 310 may obtain the trained internal structure prediction model and process the first surface data using the trained internal structure prediction model to predict the current internal structure data of the target object. In some embodiments, the input of the trained internal structure prediction model may include the first surface data of the target object, and the output may be the current internal structure data of the target object.

In some embodiments, the trained internal structure prediction model may be obtained by training an initial machine learning model. In some embodiments, the initial machine learning model may include a deep learning model. For example, the deep machine learning model may include but is not limited to one or more combinations of convolutional neural networks (CNN), regions with CNN (RCNN), Fast-RCNN, K-Nearest neighbor algorithm (KNN), support vector machines (SVM).

In some embodiments, training samples of the internal structure prediction model may include sample surface data and corresponding sample internal structure data. The sample surface data may be historical data obtained by capturing an sample object with the optical camera, and the corresponding sample internal structure data may be obtained by scanning the sample object using a medical imaging instrument (e.g., a CT device, an ultrasonic imaging device, a fluoroscopy imaging device, an MRI device). In some embodiments, the internal structure prediction model may be trained with the sample surface data as the model input and the corresponding sample internal structure data as the training label.

In some embodiments, the trained internal structure prediction model may be stored in the storage device 150 for subsequent use. In some embodiments, the internal structure prediction model may be trained by the processing device 140 or other computer devices (e.g., a computer device of the supplier of the model). In some embodiments, the internal structure prediction model learns an optimal mechanism of predicting the internal structure from plenty of training samples during the training process, which has high accuracy. The internal structure data of the target object may be predicted based on the trained internal structure prediction model and whether an anatomical image needs to be reshot may be determined based on the target object's internal and external conditions comprehensively, which can improve the determination accuracy.

In 650, historical internal structure data of the target object may be determined based on the historical anatomical image. In some embodiments, the operation 650 may be executed by the determination module 320.

In some embodiments, the historical internal structure data may reflect the internal structure condition of the target object when the historical anatomical image is captured. In some embodiments, the historical anatomical image or a portion of the historical anatomical image (e.g., a portion corresponding to a certain organ) may be regarded as the historical internal structure data. In some embodiments, a second value of the one or more internal structure parameters aforementioned may be determined based on the historical anatomical image and may be regarded as the historical internal structure data.

In 660, a second comparison result may be generated by performing a second comparison between the current internal structure data and the historical internal structure data. In some embodiments, the operation 660 may be executed by the determination module 320.

The second comparison result may reflect a difference between the internal conditions of the target object when the historical anatomical image is captured and before the treatment fraction. For example, the second comparison result may include a difference value or similarity between the current internal structure data and the historical internal structure data. Merely for example, the current internal structure data and the historical internal structure data may be images displaying an internal structure of the target object, the second comparison result may be a similarity value between the two 3D images that is within a range of 0-1, the closer the value is to 1, the more similar the two 3D images are. As another example, the current internal structure data and the historical internal structure data may be internal structure parameters of the target object, the second comparison result may be a difference value of the internal structure parameters. In some embodiments, a similarity degree between the current internal structure data and the historical internal structure data may be determined by a structural similarity index (SSIM), a Histogram-based similarity algorithm, a hash algorithm, a cosine similarity, a Jaccard similarity algorithm, etc. In some embodiments, the determination module 320 may determine first value(s) of one or more internal feature parameters based on the current internal structure data and determine second value(s) of the one or more internal feature parameters based on the historical internal structure data. Exemplary internal feature parameters may include internal structure parameters of the target object, such as the position, the shape, the size of internal organs. The determination module 320 may further determine the second comparison result by comparing the first value(s) with the second value(s). Merely for example, the second comparison result may include a difference value between the first value and the second value of an internal feature parameter.

In 670, whether an anatomical image of the target object needs to be reshot may be determined based on the first comparison result and the second comparison result.

For example, the determination module 320 may generate a first determination result of whether an anatomical image needs to be reshot based on a first comparison threshold and the first comparison result. The determination module 320 may also generate a second determination result of whether an anatomical image needs to be reshot based on a second comparison threshold and the second comparison result. For example, the determination module 320 may determine that the anatomical image does not need to be reshot only when both the first determination result and the second determination result show that the anatomical image does not need to be reshot; on the contrary, the determination module 320 may determine that the anatomical image needs to be reshot. In some embodiments, the first comparison threshold and the second comparison threshold may be determined based on relevant information of the region of interest in the target object and/or relevant information of the target object. Since the acceptable changes in the body condition of the target object in different treatment scenarios (e.g., different sizes of tumor, different positions of tumor) are different, the first comparison threshold and the second comparison threshold may be determined according to the actual condition of the patient to improve the accuracy of judgment.

As another example, the determination module 320 may determine a first difference between the first comparison result and the first comparison threshold. The determination module 320 may determine a second difference between the second comparison result and the second comparison threshold. The determination module 320 may further determine whether an anatomical image needs to be reshot based on the first difference and the second difference. For example, the determination module 320 may perform a weighted sum of the first difference and the second difference to comprehensively determine whether an anatomical image needs to be reshot. A weight of the first difference and a weight of the second difference may be determined according to different treatment scenarios (e.g., different sizes of tumors, different locations of tumors) and different acceptable body change conditions of the patient.

In some embodiments, the second surface data of the target object may be determined when the historical anatomical image is collected based on the historical anatomical image, and the second surface data may be compared with the first surface data obtained by the optical camera before the current treatment fraction to determine a difference of the body surface conditions of the target object before the current treatment fraction and when the historical anatomical image is captured. Meanwhile, a difference between the internal conditions of the target object before the current treatment fraction and when the historical anatomical image is captured may be determined by comparing the current internal structure data and the historical internal structure data. By evaluating the change of the internal condition and the body surface condition comprehensively, the accuracy of determining whether an anatomical image needs to be reshot may be effectively improved, and the accuracy and safety of radiation therapy may be improved.

In some embodiments, the target object may receive one or more historical treatment fractions before the current treatment fraction. Whether an anatomical image needs to be reshot may be determined by analyzing a changing trend of the body surface condition of the target object during the whole treatment process.

In some embodiments, the obtaining module 210 may obtain a plurality groups of third surface data corresponding to a plurality of historical treatment fractions, each group of third surface data may reflect the body surface condition of the target object before one historical treatment fraction. The third surface data may be surface data obtained before the plurality of historical treatment fractions by optical detection method. In some embodiments, the obtaining manner of the third surface data may be similar to the obtaining manner of the first surface data, which is not repeated here.

In some embodiments, the determination module 220 may generate a plurality of third comparison results by comparing the second surface data with each group of the plurality groups of third surface data. The determination module 220 may determine whether an anatomical image of the target object needs to be reshot based on the first comparison result and the plurality of third comparison results. For example, the historical anatomical image may be a CT image collected in the planning stage, the second surface data may reflect the body surface condition of the target object in the planning stage. A difference between the body surface condition of the target object during a historical treatment fraction and the body surface condition of the target object during the planning stage may be determined by comparing the second surface data with the third surface data corresponding to the historical treatment fraction. Therefore, based on the first comparison result and the third comparison result, a changing trend of the difference between the body surface condition of the target object during the planning stage and the body surface condition of the target object during the whole treatment process may be determined, and whether an anatomical image needs to be reshot may be further determined. Merely for example, although the comparison results corresponding to the historical treatment fraction and the current treatment fraction do not exceed the first comparison threshold, if the body surface condition of the target object tends to deviate from the body surface condition in the planning stage (e.g., the first comparison result and the third comparison result show that the offsets of the points on the target object gradually increase), the body of the target object may constantly undergo a change. Alternatively, compared with the historical treatment fraction, if the body surface condition of the target object during the current treatment fraction obviously deviates from the surface condition of the historical planning stage (e.g., the offsets of the points on the target object in the first comparison result is obviously greater than the offsets corresponding to the previous treatment fraction), the body of the target object may undergo or be about to undergo a major change. In such cases, in order to avoid the effect caused by the body change of the target object, an anatomical image needs to be reshot.

In some embodiments, the determination module 220 may sort the first surface data and the plurality groups of third surface data according to the collection time, and generate a fourth comparison result by comparing the surface data corresponding to each pair of adjacent treatment fractions. For example, if the $n^{th}$ treatment fraction is the current treatment fraction, and the corresponding surface data may be recorded as Sn; the surface data corresponding to the first historical treatment fraction to the $n-1^{th}$ historical treatment fraction may be recorded as S1-Sn-1. The determination module 220 may determine a difference D1 between S1 and S2, a difference D2 between S2 and S3, . . . , and a difference Dn-1 between Sn-1 and Sn. Based on the difference D1-Dn-1, a changing trend of the target object may be determined to determine whether an anatomical image needs to be reshot. For example, if a difference value between the difference Dn-1 and an average of D1-Dn-2 is greater than a threshold, the target object may undergo or be about to undergo a major change, it may be determined that an anatomical image of the target object needs to be reshot.

It should be noted that the above description of process 600 is merely provided for illustration purposes, and does not limit the scope of the present disclosure. For those skilled in the art, various modifications and changes can be made to the process 600 under the guidance of the present disclosure. However, these amendments and changes are still within the scope of the present disclosure. For example, the operations 640 and 650 may be performed synchronously. As another example, the determination module 140 may determine whether an anatomical image of the target object needs to be reshot comprehensively based on two or more of the first comparison result, the second comparison result, the third comparison result, and the fourth comparison result.

Figure 7:
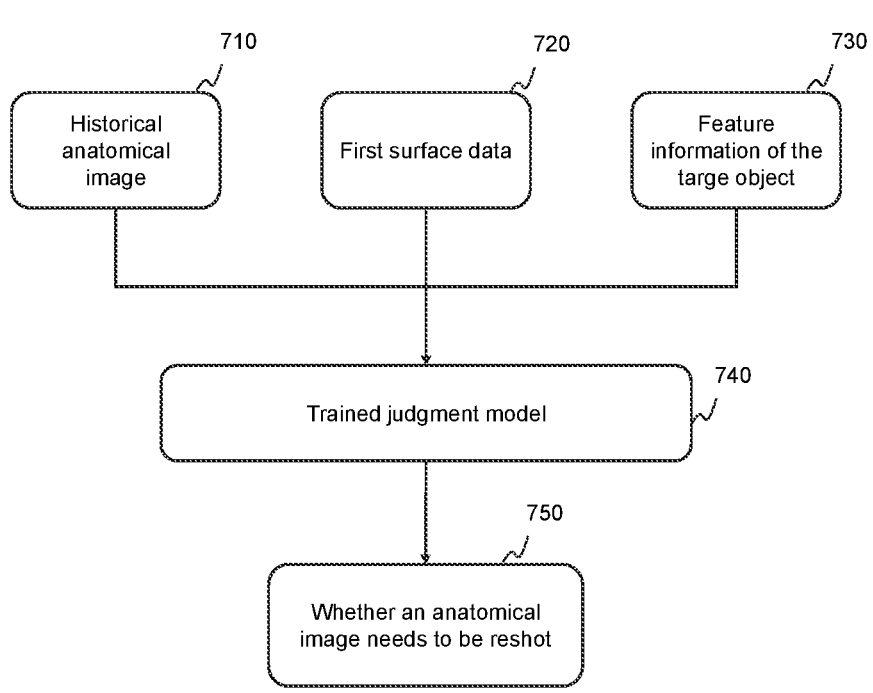
FIG. 7 is a flowchart illustrating an exemplary process for radiation therapy guidance according to some embodiments of the present disclosure.

FIG. 7 is a flowchart illustrating an exemplary process for radiation therapy guidance according to some embodiments of the present disclosure. In some embodiments, one or more operations of the process 700 may be executed to implement at least part of operation 430 in FIG. 4.

In 710, historical anatomical image of the target object may be obtained. In some embodiments, the operation 710 may be executed by the obtaining module 310. More descriptions of the acquisition of the historical anatomical image may be found in the operation 420, which is not repeated here.

In 720, first surface data of the target object may be obtained. In some embodiments, the operation 710 may be executed by the obtaining module 310 and/or the determination module 320. More descriptions of the acquisition of the first surface data may be found in the operation 410, which is not repeated here.

In 730, feature information of the target object may be obtained. In some embodiments, the operation 720 may be executed by the obtaining module 310.

The feature information of the target object may be information that reflects the body condition of the target object. In some embodiments, the feature information of the target object may include the tumor type of the target object, shape information (e.g., the height, the fatness, etc.) of the target object, etc. In some embodiments, the feature information of the target object may further include the intensity of the target object's response to the treatment, which may affect the judgment result of whether an anatomical image needs to be reshot. In some embodiments, the obtaining module 310 may obtain the feature information of the target object from the storage device 150 or an external storage device.

In 740, a trained judgment model may be obtained. In some embodiments, the operation 720 may be executed by the obtaining module 310.

In some embodiments, the obtaining module 310 may obtain the trained judgment model stored in the storage device 150. The judgment model may determine a judgment result of whether an anatomical image needs to be reshot or a probability that an anatomical image needs to be reshot based on the input of the model. In some embodiments, the trained judgment model may be obtained by training an initial machine learning model. In some embodiments, the machine learning model may include a deep learning model described elsewhere in the present disclosure.

In some embodiments, training samples of the judgment model may include a plurality groups of historical sample data, each group of the historical sample data may include feature information of a sample patient, an anatomical image of the sample patient, first surface data of the sample patient, and a judgment result of whether an anatomical image needs to be reshot of the sample patient. The obtaining manner of the feature information of sample patient, the anatomical image of the sample patient, and the first surface data of the sample patient may be similar to the obtaining manner of the feature information of the target object, the anatomical image of the target object, and the first surface data of the target object, which is not repeated here. The judgment result of whether an anatomical image of the sample patient needs to be reshot may be determined manually, or preliminarily determined through the descriptions of FIGS. 4-6 and then manually confirmed or corrected. In some embodiments, the initial machine learning model may be trained with the feature information of sample patient, the anatomical image of the sample patient, and the first surface data of the sample patient as the model input and a corresponding judgment result as the training label. In some embodiments, the trained judgment model may be stored in the storage device 150 for subsequent use. In some embodiments, the trained judgment model may be trained by the processing device 140 or other computer devices (e.g., a computer device of the supplier of the model).

In some embodiments, for different treatment portions (e.g., a tumor portion), different candidate judgment models may be trained, i.e., each treatment portion may correspond to a judgment model. For example, a lung tumor judgment model may be trained for a lung tumor, a stomach tumor judgment model may be trained for a stomach tumor. In some embodiments, the processing device 140 or other computer devices (e.g., a computer device of the supplier of the judgment model) may train a candidate judgment model corresponding to each treatment portion in advance and store the candidate judgment models in the storage device 150. When determining whether an anatomical image needs to be reshot for the target object, the obtaining module 310 may obtain at least two candidate judgment models corresponding to at least two body portions to be treated from the storage device 150. The obtaining module 3'0 may select a judgment model corresponding to the body portion to be treated of the target object from the at least two candidate judgment models based on the portion of the target object to be treated.

In some embodiments, for different treatment portions (i.e., a tumor portion), the radiation therapy guidance system may use a same general judgment model, the obtaining module 310 may obtain the trained general judgment model from the storage device 150 directly.

In some embodiments, the more the training samples of the judgment model, the higher the accuracy of the judgment model. Therefore, the radiation therapy guidance system may obtain new historical sample data constantly to update the judgment model.

In 750, whether an anatomical image of the target object needs to be reshot for the treatment fraction may be determined by processing the feature information of the target object, the historical anatomical image, and the first surface data using the trained judgment model.

For example, the determination module 320 may input the feature information, the historical anatomical image, and the first surface data of the target object into the trained judgment model, the trained judgment model may output a judgment result of whether an anatomical image of the target object needs to be reshot for the treatment fraction directly. Alternatively, the trained judgment model may output a probability that an anatomical image of the target object needs to be reshot for the treatment fraction, the determination module 320 may determine whether an anatomical image needs to be reshot based on the probability. Merely for example, when the probability is greater than a specific threshold, it may be determined that the anatomical image needs to be reshot.

In some embodiments, if different treatment portions use a same trained judgment model, the determination module 320 may adjust a judge threshold of the judgment model. The judgment threshold may be a parameter of a judgment layer (e.g., a full connection layer) in the judgment model, which is used to be compared with the probability that an anatomical image needs to be reshot to output the judgment result of whether an anatomical image needs to be reshot.

In some embodiments, the determination module 320 may adjust the judgment threshold of the judgment model based on the body portion to be treated of the target object. Since the acceptance levels of the change in the body change condition of the patient in different treatment scenarios (e.g., different sizes of tumor, different positions of tumor) are different, the determination module 320 may improve the accuracy of the judgment by adjusting the judgment threshold of the judgment model. For example, different body portions to be treated may correspond to different judgment thresholds, a relatively strict judgment threshold may be set for the portions (e.g., head) that have a great impact on the body of the patient, at this time, the judgment model may allow a small difference between the condition of the target object when the historical anatomical is captured and when the first surface data is captured. A relatively loose judgment threshold may be set for the portions that have a low impact on the body of the patient, at this time, the judgment model may allow a relatively bigger difference between the condition of the target object when the historical anatomical image is captured and when the first surface data is captured.

In some embodiments, the determination module 320 may determine whether an anatomical image of the target object needs to be reshot for the treatment fraction by processing the feature information of the target object, the historical anatomical image, and the first surface data using the adjusted judgment model.

In some embodiments, determining whether an anatomical image of the target object needs to be reshot for the treatment fraction directly based on the relevant information using the trained judgment model may simplify the radiation therapy guidance process without performing multiple judgments, which has higher judgment efficiency.

It should be noted that the above description of process 700 is merely provided for illustration purposes, and does not limit the scope of the present disclosure. For those skilled in the art, various modifications and changes can be made to the process 700 under the guidance of the present disclosure. However, these amendments and changes are still within the scope of the present disclosure. For example, the operations 710, 720, and 730 may be performed synchronously.

The possible beneficial effects of the embodiments of the present disclosure may include but may not be limited to: (1) the body surface features of a patient may be observed with high accuracy by optical detection methods, which can improve the accuracy of radiation therapy guidance. In addition, this manner may detect the body surface features of the patient fast without bringing additional radiations, reduce the radiation damage to the patient, and have a relatively high security and practicality; (2) the whole-body registration may be performed on the first surface data and the second surface data firstly, then the local data corresponding to the region of interest may be registered, which can eliminate and reduce the effect caused by the body positioning or posture, so that an accurate difference between the conditions of the region of interest of the target object before the treatment fraction and when the historical anatomical image is captured may be determined; (3) during the process of comparing the first surface data with the second surface, the comparison threshold may be determined based on the second judgment model trained using historical judgment samples, which improves the accuracy of surface data comparison; (4) the first surface data and the second surface data may be preprocessed before the comparison, or the first comparison result may be corrected after comparing the first surface data with the second surface data, which can reduce the effect of the physiological motion of the target object and improve the accuracy of the surface data comparison; (5) the internal structure data of the target object may be predicted and whether an anatomical image needs to be reshot may be judged based on the patient's internal and external conditions comprehensively, which can improve the determination accuracy; (6) whether an anatomical image of the target object needs to be reshot for the treatment fraction can be determined directly based on the relevant information using the trained judgment model, which may simplify the radiation therapy guidance process and improve the determination efficiency.

In some embodiments, a process (e.g., the process 400) described above may be executed by a processing device (e.g., a processing device 140). For example, the process 400 may be implemented as a set of instructions (e.g., application program) stored in a storage device 150 or a storage device external to the system 100. In some embodiments, the processing device 140 may execute the set of instructions and accordingly be directed to perform the process. The operations of the process presented above are intended to be illustrative. In some embodiments, the process may be accomplished with one or more additional operations not described and/or without one or more of the operations discussed. Additionally, the order of the operations of process illustrated in figures and described above is not intended to be limiting The basic concepts have been described. Obviously, for those skilled in the art, the detailed disclosure may be only an example and may not constitute a limitation to the present disclosure. Although not explicitly stated here, those skilled in the art may make various modifications, improvements, and amendments to the present disclosure. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of the specification are not necessarily all referring to the same embodiment. In addition, some features, structures, or features in the present disclosure of one or more embodiments may be appropriately combined.

Moreover, unless otherwise specified in the claims, the sequence of the processing elements and sequences of the present application, the use of digital letters, or other names are not used to define the order of the application flow and methods. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various assemblies described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure and aiding in the understanding of one or more of the various embodiments. However, this disclosure may not mean that the present disclosure object requires more features than the features mentioned in the claims. In fact, the features of the embodiments are less than all of the features of the individual embodiments disclosed above.

In some embodiments, numbers describing the number of ingredients and attributes are used. It should be understood that such numbers used for the description of the embodiments use the modifier "about", "approximately", or "substantially" in some examples. Unless otherwise stated, "about", "approximately", or "substantially" indicates that the number is allowed to vary by ±20%. Correspondingly, in some embodiments, the numerical parameters used in the description and claims are approximate values, and the approximate values may be changed according to the required characteristics of individual embodiments. In some embodiments, the numerical parameters should consider the prescribed effective digits and adopt the method of general digit retention. Although the numerical ranges and parameters used to confirm the breadth of the range in some embodiments of the present disclosure are approximate values, in specific embodiments, settings of such numerical values are as accurate as possible within a feasible range.

For each patent, patent application, patent application publication, or other materials cited in the present disclosure, such as articles, books, specifications, publications, documents, or the like, the entire contents of which are hereby incorporated into the present disclosure as a reference. The application history documents that are inconsistent or conflict with the content of the present disclosure are excluded, and the documents that restrict the broadest scope of the claims of the present disclosure (currently or later attached to the present disclosure) are also excluded. It should be noted that if there is any inconsistency or conflict between the description, definition, and/or use of terms in the auxiliary materials of the present disclosure and the content of the present disclosure, the description, definition, and/or use of terms in the present disclosure is subject to the present disclosure.

At last, it should be understood that the embodiments described in the disclosure are used only to illustrate the principles of the embodiments of this application. Other modifications may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A method for radiation therapy guidance implemented on at least one processor, comprising:

obtaining first surface data of a target object to be treated by using an optical camera, wherein the first surface data reflects the body surface condition of the target object before a treatment fraction;

obtaining a historical anatomical image of the target object;

determining second surface data of the target object based on the historical anatomical image, wherein the second surface data reflects the body surface condition of the target object when the historical anatomical image is captured;

generating a first comparison result by comparing the first surface data with the second surface data; and determining whether an anatomical image of the target object needs to be reshot for the treatment fraction based on the first comparison result by:

determining a comparison threshold based on a judgment model, the judgment model being a trained classification model; and determining whether an anatomical image of the target object needs to be reshot based on the first comparison result and the comparison threshold.

2. The method of claim 1, wherein the target object undergoes physiological motion, the optical camera is configured to capture a plurality of first frames of the target object before the treatment fraction, the first surface data is determined based on a target first frame in the plurality of first frames, the historical anatomical image includes a plurality of second frames, the second surface data is determined based on a target second frame in the plurality of second frames, and the target first frame and the target second frame correspond to a same physiological motion phase relating to the physiological motion.

3. The method of claim 1, wherein the target object undergoes physiological motion, the determining whether an anatomical image of the target object needs to be reshot for the treatment fraction based on the first comparison result includes:

obtaining a deformation model relating to the physiological motion, wherein the deformation model reflects a movement process of the target object or a portion of target object due to the physiological motion;

obtaining a corrected comparison result by correcting the first comparison result based on the deformation model; and determining whether an anatomical image of the target object needs to be reshot for the treatment fraction based on the corrected comparison result.

4. The method of claim 1, wherein training samples of the judgment model include:

first sample surface data and second sample surface data of a positive sample object that needs to be reshot; and third sample surface data and fourth sample surface data of a negative sample object that does not need to be reshot.

5. The method of claim 1, wherein the generating a first comparison result by comparing the first surface data with the second surface data includes:

registering the first surface data and the second surface data;

determining first local data and second local data corresponding to a region of interest of the target object from the registered first surface data and the registered second surface data, respectively; and generating the first comparison result by comparing the first local data with the second local data.

6. The method of claim 1, wherein the determining whether an anatomical image of the target object needs to be reshot for the treatment fraction based on the first comparison result includes:

predicting current internal structure data of the target object based on the first surface data;

determining historical internal structure data based on the historical anatomical image;

generating a second comparison result by comparing the current internal structure data and the historical internal structure data;

determining whether an anatomical image of the target object needs to be reshot for the treatment fraction based on the first comparison result and the second comparison result.

7. The method of claim 6, wherein the predicting current internal structure data of the target object based on the first surface data includes:

obtaining a trained internal structure prediction model; and predicting the current internal structure data of the target object by processing the first surface data using the trained internal structure prediction model.

8. The method of claim 1, wherein the determining whether an anatomical image of the target object needs to be reshot for the treatment fraction based on the first comparison result includes:

obtaining a plurality groups of third surface data corresponding to a plurality of historical treatment fractions, each group of third surface data reflecting the body surface condition of the target object before one of the plurality of historical treatment fractions;

generating a plurality of third comparison results by comparing each group of third surface data with the second surface data; and determining whether an anatomical image of the target object needs to be reshot for the treatment fraction based on the first comparison result and the plurality of third comparison results.

9. The method of claim 1, further including:

obtaining initial surface data of the target object captured by the optical camera;

obtaining a target reference model from a reference database based on feature information of the target object, the reference database storing a plurality of reference models corresponding to a plurality of types of objects; and determining the first surface data by correcting the initial surface data based on the target reference model.

10. The system of claim 8, wherein the historical anatomical image is an image collected in a planning stage, and whether an anatomical image of the target object needs to be reshot for the treatment fraction is determined based on the first comparison result and the plurality of third comparison results by:

determining, based on the first comparison result and the third comparison result, a changing trend of a difference between a body surface condition of the target object during the planning stage and a body surface condition of the target object during a treatment process; and in response to determining that the changing trend indicates that the body surface condition during the treatment process tends to deviate from the body surface condition in the planning stage, determining that an anatomical image needs to be reshot.

11. The system of claim 1, wherein the historical anatomical image is an image collected in a planning stage, and the determining whether an anatomical image of the target object needs to be reshot for the treatment fraction based on the first comparison result includes:

obtaining a plurality groups of third surface data corresponding to a plurality of historical treatment fractions, each group of third surface data reflecting the body surface condition of the target object before one of the plurality of historical treatment fractions;

generating a fourth comparison result by comparing surface data corresponding to each pair of adjacent treatment fractions among the first surface data and the plurality of groups of third surface data;

determining, based on the fourth comparison result, a changing trend of the target object; and determining, based on the changing trend of the target object, whether an anatomical image needs to be reshot.

12. A system for radiation therapy guidance, comprising:

at least one storage device including a set of instructions; and at least one processor configured to communicate with the at least one storage device, wherein when executing the set of instructions, the at least one processor is configured to cause the system to perform operations including:

obtaining first surface data of a target object to be treated by using an optical camera, wherein the first surface data reflects the body surface condition of the target object before a treatment fraction;

obtaining a historical anatomical image of the target object;

determining second surface data of the target object based on the historical anatomical image, wherein the second surface data reflects the body surface condition of the target object when the historical anatomical image is captured;

generating a first comparison result by comparing the first surface data with the second surface data; and determining whether an anatomical image of the target object needs to be reshot for the treatment fraction based on the first comparison result by:

obtaining a plurality groups of third surface data corresponding to a plurality of historical treatment fractions, each group of third surface data reflecting the body surface condition of the target object before one of the plurality of historical treatment fractions;

generating a plurality of third comparison results by comparing each group of third surface data with the second surface data; and determining whether an anatomical image of the target object needs to be reshot for the treatment fraction based on the first comparison result and the plurality of third comparison results.

13. The system of claim 12, wherein the target object undergoes physiological motion, the optical camera is configured to capture a plurality of first frames of the target object before the treatment fraction, the first surface data is determined based on a target first frame in the plurality of first frames, the historical anatomical image includes a plurality of second frames, the second surface data is determined based on a target second frame in the plurality of second frames, and the target first frame and the target second frame correspond to a same physiological motion phase relating to the physiological motion.

14. The system of claim 12, wherein the target object undergoes physiological motion, and to determine whether an anatomical image of the target object needs to be reshot for the treatment fraction based on the first comparison result, the at least one processor is further configured to cause the system to perform operations including:

obtaining a deformation model relating to the physiological motion, wherein the deformation model reflects a movement process of the target object or a portion of target object due to the physiological motion;

obtaining a corrected comparison result by correcting the first comparison result based on the deformation model; and determining whether an anatomical image of the target object needs to be reshot for the treatment fraction based on the corrected comparison result.

15. The system of claim 12, wherein to generate a first comparison result by comparing the first surface data with the second surface data, the at least one processor is further configured to cause the system to perform operations including:

registering the first surface data and the second surface data;

determining first local data and second local data corresponding to a region of interest of the target object from the registered first surface data and the registered second surface data, respectively; and generating the first comparison result by comparing the first local data with the second local data.

16. The system of claim 12, wherein to determine whether an anatomical image of the target object needs to be reshot for the treatment fraction based on the first comparison result, the at least one processor is further configured to cause the system to perform operations including:

predicting current internal structure data of the target object based on the first surface data;

determining historical internal structure data based on the historical anatomical image;

generating a second comparison result by comparing the current internal structure data and the historical internal structure data;

determining whether an anatomical image of the target object needs to be reshot for the treatment fraction based on the first comparison result and the second comparison result.

17. A method for radiation therapy guidance implemented on at least one processor, comprising:

obtaining first surface data of a target object to be treated by using an optical camera, wherein the first surface data reflects the body surface condition of the target object before a treatment fraction;

obtaining a historical anatomical image of the target object;

obtaining feature information of the target object;

obtaining a trained determination model; and determining whether an anatomical image of the target object needs to be reshot for the treatment fraction by processing the feature information of the target object, the historical anatomical image, and the first surface data using the trained determination model.

* * * * *